(12) United States Patent
Wu et al.

(10) Patent No.: US 10,475,538 B2
(45) Date of Patent: Nov. 12, 2019

(54) SYSTEM FOR PREDICTING COMPUTED TOMOGRAPHY DATA FROM SURFACE DATA

(71) Applicant: Siemens Healthcare GmbH, Erlangen (DE)

(72) Inventors: Yifan Wu, Philadelphia, PA (US);
Vivek Kumar Singh, Princeton, NJ (US); Kai Ma, Princeton, NJ (US);
Terrence Chen, Princeton, NJ (US);
Birgi Tamersoy, Erlangen (DE);
Jiangping Wang, Plainsboro, NJ (US);
Andreas Krauss, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 156 days.

(21) Appl. No.: 15/867,786

(22) Filed: Jan. 11, 2018

(65) Prior Publication Data
US 2019/0214135 A1 Jul. 11, 2019

(51) Int. Cl.
*G06K 9/00* (2006.01)
*G16H 50/20* (2018.01)
(Continued)

(52) U.S. Cl.
CPC .......... *G16H 50/20* (2018.01); *G06T 7/0014* (2013.01); *G16H 30/40* (2018.01); *A61B 6/032* (2013.01); *G06T 2207/10081* (2013.01); *G06T 2207/20081* (2013.01); *G06T 2207/30008* (2013.01); *G06T 2207/30061* (2013.01)

(58) Field of Classification Search
None
See application file for complete search history.

(56) References Cited

U.S. PATENT DOCUMENTS

2017/0337682 A1* 11/2017 Liao .................. G06T 7/30
2018/0260957 A1* 9/2018 Yang .................. G06T 7/0012
(Continued)

OTHER PUBLICATIONS

Nie, Dong, et al. "Medical image synthesis with context-aware generative adversarial networks." International Conference on Medical Image Computing and Computer-Assisted Intervention. Springer, Cham, 2017. (Year: 2017).*

(Continued)

*Primary Examiner* — Samah A Beg (57) ABSTRACT

A system and method includes operation of a generation network to generate first generated computed tomography data based on a first instance of surface data, determination of a generation loss based on the first generated computed tomography data and on a first instance of computed tomography data which corresponds to the first instance of surface data, operation of a discriminator network to discriminate between the first generated computed tomography data and the first instance of computed tomography data, determination of a discriminator loss based on the discrimination between the first generated computed tomography data and the first instance of computed tomography data, determination of discriminator gradients of the discriminator network based on the discriminator loss, and updating of weights of the generation network based on the generation loss and the discriminator gradients.

20 Claims, 10 Drawing Sheets

(51) Int. Cl.
*G16H 30/40* (2018.01)
*G06T 7/00* (2017.01)
*A61B 6/03* (2006.01)

(56) References Cited

U.S. PATENT DOCUMENTS

| | | | |
|---|---|---|---|
| 2019/0057521 A1* | 2/2019 | Teixeira | G06K 9/6262 |
| 2019/0216409 A1* | 7/2019 | Zhou | G06T 11/003 |
| 2019/0220701 A1* | 7/2019 | Novak | G06K 9/6256 |
| 2019/0223819 A1* | 7/2019 | Mansi | G06N 20/00 |

OTHER PUBLICATIONS

Neff, Thomas, et al. "Generative adversarial network based synthesis for supervised medical image segmentation." Proc. OAGM and ARW Joint Workshop. 2017. (Year: 2017).*

Goodfellow, Ian J. et al., "Generative Adversarial Nets", Department of Computer and Operational Research, University of Montreal, Jun. 10, 2014, 9 pp.

Isola, Phillip et al, "Image-to-Image Translation with Conditional Adversarial Networks", AI Research (BAIR) Laboratory, UC Berkeley, Nov. 22, 2017, 17 pp.

Kingma, Diederik P. et al., "ADAM: A Method for Stochastic Optimization", International Conference of Learning Representations, 2015, 15 pp.

Long, Jonathan et al., "Fully Convolutional Networks for Semantic Segmentation", UC Berkeley, 10 pp, 2015.

Ronneberger, Olaf et al., "U-Net: Convolutional Networks for Biomedical Image Segmentation", Computer Science Department and BIOSS Centre for Biological Signalling Studies, University of Freiburg, Germany, May 18, 2015, 8 pp.

Singh, Vivek et al, "DARWIN: Deformable Patient Avatora Representation With Deep Image Network", Medical Imaging Technologies, Siemens Medical Solutions USA Inc., Princeton, NJ, USA, Siemens Healthcare GmbH, Forcheim, Germany, 8 pp, Sep. 2017.

Ulyanov, Dmitry et al., "Instance Normalization: The Missing Ingredient for Fast Stylization", Nov. 6, 2017, 6 pp.

Xie, Saining et al., "Holistically-Nested Edge Detection", Department of CSE and Department of CogSci, University of California, San Diego, Oct. 4, 2015, 10 pp.

* cited by examiner

SYSTEM FOR PREDICTING COMPUTED TOMOGRAPHY DATA FROM SURFACE DATA

BACKGROUND

Computed Tomography (CT) data depicting internal patient structures may be used for diagnosis, dose planning and patient positioning. Acquisition of CT data is time-consuming and exposes a patient to potentially harmful radiation. Accordingly, some conventional systems obtain surface data using a surface-scanning camera, identify anatomical landmarks based on the surface data, and position a patient based on the landmarks. Such positioning is not as accurate as positioning based on CT data, and these conventional systems do not alleviate the need for CT data in diagnosis or dose planning.

It has been considered to utilize neural networks to generate CT data based on skin surface data, formulated as a per-pixel classification or regression. These formulations treat each output pixel as conditionally-independent and therefore fail to capture structure information in the output space. What is needed is a network design and training architecture which provides suitable CT data from skin surface data.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide a network and training architecture to predict volumetric CT data based on surface data. Such predictions may be useful for scan planning, dose planning, and registration with data from other modalities (e.g., X-ray, ultrasound).

Figure 1:
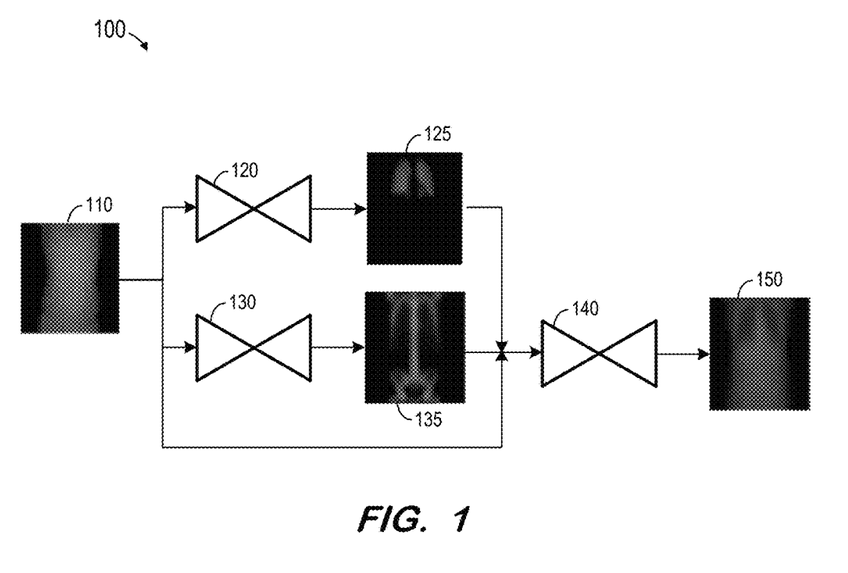
FIG. 1 is a block diagram of a system to predict computed tomography data based on surface data according to some embodiments.

FIG. 1 depicts network architecture 100 according to some embodiments. Network architecture 100 includes lung mask regression network 120, bone mask regression network 130, and CT data generation network 140. As illustrated, CT surface data 110 (or other volumetric surface data) is input in parallel to lung mask regression network 120 and bone mask regression network 130. Lung mask regression network 120 outputs volumetric lung mask 125 and bone mask regression network 130 outputs volumetric bone mask 135. Generation network 140 receives volumetric lung mask 125, volumetric bone mask 135 and original surface data 110 and generates predicted volumetric CT data 150. Embodiments may employ more or other regression networks to generate other masks for input to generation network 140.

As will be described below, networks 120, 130 and 140 may be trained using regression algorithms. Some embodiments further employ end-to-end training of the networks using a novel dual-conditional generative adversarial network training architecture.

Figure 2:
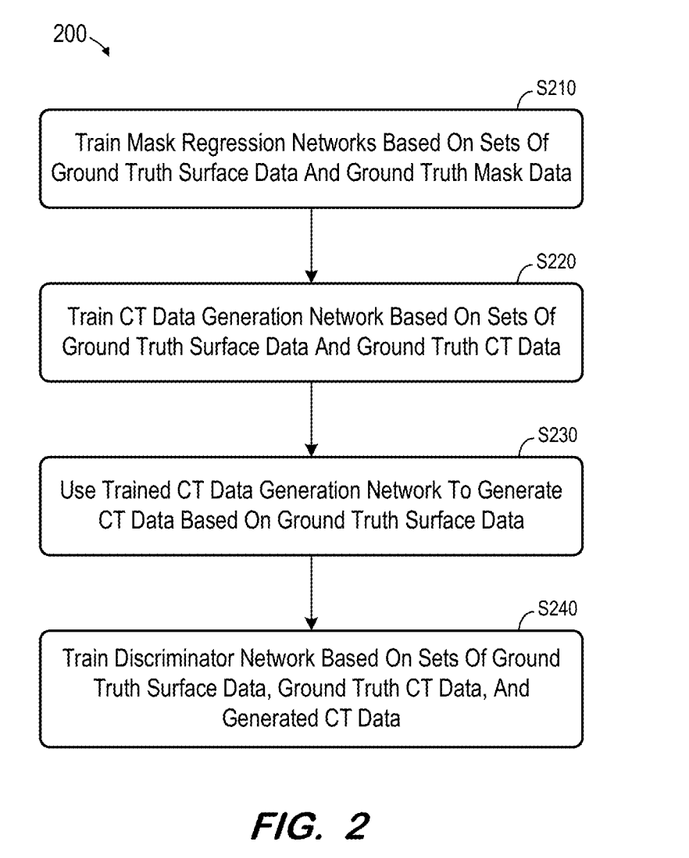
FIG. 2 is a flow diagram of a network training process according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Embodiments are not limited to the examples described below.

Initially, one or more mask regression networks are trained at S210. Each mask regression network is trained based on sets of "ground truth" surface data and ground truth mask data corresponding to the particular mask regression network being trained. According to some embodiments, the mask regression networks trained at S210 include a lung mask regression network and a bone mask regression network. Embodiments are not limited to two mask regression networks or to lung masks and bone masks. For instance, regression networks can be added to generate masks for various organs (such as kidneys, heart, liver). Furthermore, besides organs and bone masks, regression networks may be used to predict masks for muscle density or distribution of subcutaneous body fat.

Figure 3:
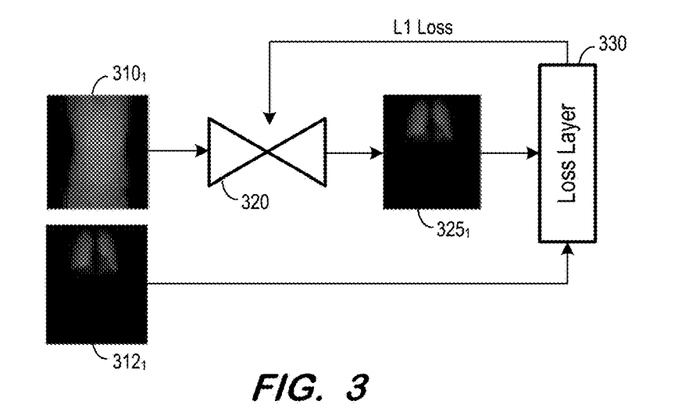
FIG. 3 is a block diagram illustrating training of a regression network to generate a lung mask from surface data according to some embodiments.

FIG. 3 illustrates training of a lung mask regression network according to some embodiments of S210. Lung mask regression network 320 is designed to receive three-dimensional surface data and output a three-dimensional lung mask. Training of lung mask regression network 320 is based on sets of data such as ground truth surface data $310_1$ and ground truth lung mask $312_1$. According to some embodiments, ground truth surface data $310_1$ and ground truth lung mask $312_1$ were generated from a same CT scan of a patient. In this regard, ground truth surface data $310_1$ may comprise volumetric data in which a voxel is associated with a value of 1 if it is located within the body, and a value of 0 if it is outside the body. The voxels of ground truth lung mask $312_1$ are equal to 1 if they are located within a lung (as determined from the CT scan), and 0 otherwise.

During training, network 320 receives ground truth surface data $310_1$ and outputs lung mask $325_1$. Loss layer 330 determines an L1 loss based on a difference between lung mask $325_1$ and ground truth lung mask $312_1$. The L1 loss may be determined as the sum of absolute differences between values of corresponding voxels of lung mask $325_1$ and ground truth lung mask $312_1$. The L1 loss is back-propagated to network 320 to change the internal weights thereof as is known in the art. This process continues with many additional sets of data (e.g., ground truth surface data instances $310_{2\to n}$ and corresponding ground truth lung mask instances $312_{2\to n}$) until the L1 loss across the entire input dataset reaches an acceptable level, as is also known in the art.

Figure 4:
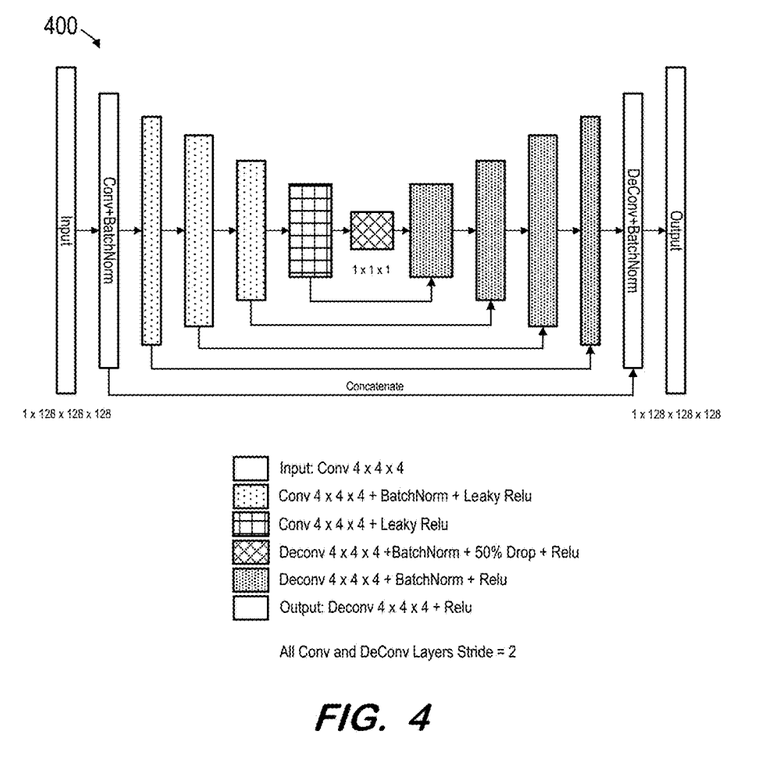
FIG. 4 illustrates a network architecture according to some embodiments.

FIG. 4 illustrates architecture 400 of network 320 according to some embodiments. Architecture 400 encodes the original input size to a 1×1×1 bottleneck. The number of filters after the first convolution layer is thirty-two, which is doubled after each following convolution layer and divided by two after each deconvolution layer.

Figure 5:
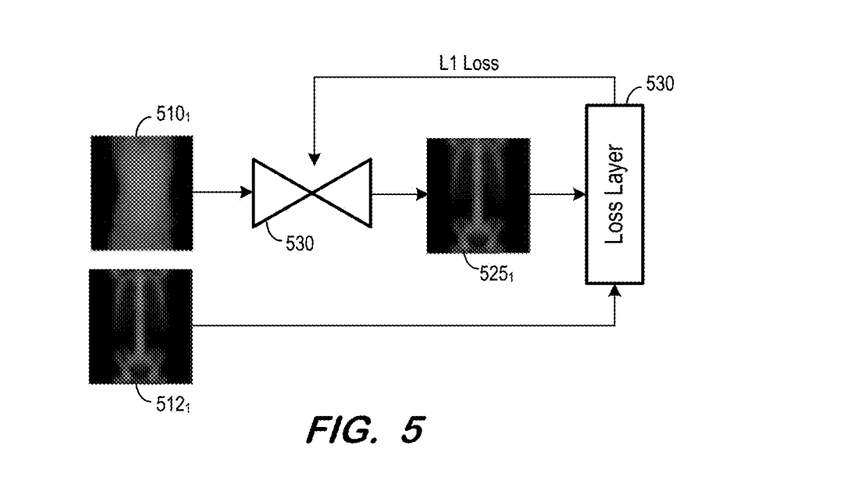
FIG. 5 is a block diagram illustrating training of a regression network to generate a bone mask according to some embodiments.

FIG. 5 illustrates training of a bone mask regression network at S210 according to some embodiments. Bone mask regression network 530 receives ground truth surface data $510_1$ and outputs bone mask $525_1$. Loss layer 530 determines an L1 loss based on a difference between bone mask $525_1$ and ground truth bone mask $512_1$. The L1 loss is back-propagated to network 520 to change the internal weights thereof as is known in the art, and the process repeats over many sets of surface data and bone mask instances until a satisfactory L1 loss is achieved. As described with respect to FIG. 3, ground truth surface data $510_1$ and ground truth bone mask $512_1$ may have been generated from a same CT scan of a patient, where the voxels of ground truth bone mask $512_1$ are equal to 1 if they are located within bone (as determined from the CT scan), and 0 otherwise.

Figure 6:
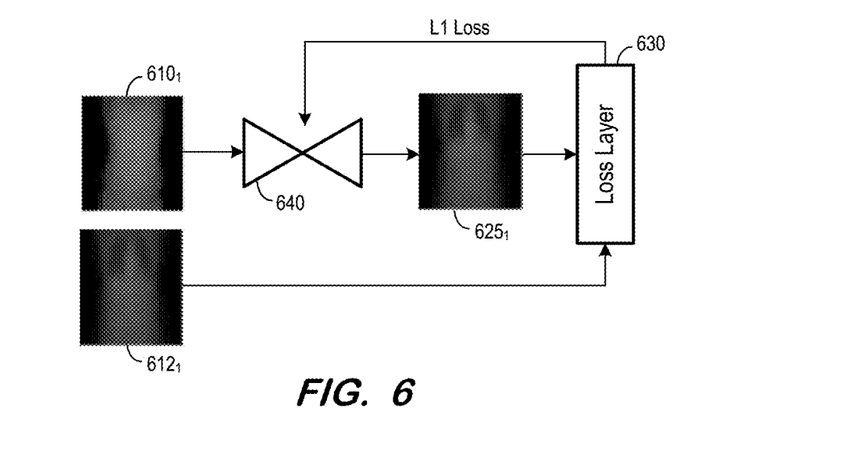
FIG. 6 is a block diagram illustrating training of a generation network to generate CT data according to some embodiments.

Next, at S220, a CT data generation network is trained based on sets of ground truth surface data and ground truth CT data. FIG. 6 illustrates training of CT data generation network according to some embodiments of S220. As shown, CT data generation network 640 receives ground truth surface data $610_1$ and outputs CT data $625_1$. Loss layer 630 determines an L1 loss based on a difference between CT data $625_1$ and ground truth CT data $612_1$ corresponding to ground truth surface data $610_1$. The L1 loss is back-propagated to network 640 to change the internal weights of network 640, and the process repeats over many sets of surface data and CT data (e.g., ground truth surface data instances $610_{2\to n}$ and corresponding ground truth CT data instances $612_{2\to n}$) until a satisfactory L1 loss is achieved.

Training of the mask regression networks and generation network at S210 and S220 may also comprise testing based on data which is different from the data used to train the networks. If the testing results are unsatisfactory, training may resume using a modified network architecture, different training data and/or different weightings.

Regression network 530 and/or generation network 640 may be implemented by architecture 400 in some embodiments. Embodiments are not limited to the FIG. 4 architecture, or to the use of an identical network architecture for two or more of the mask regression and generation networks.

Figure 7:
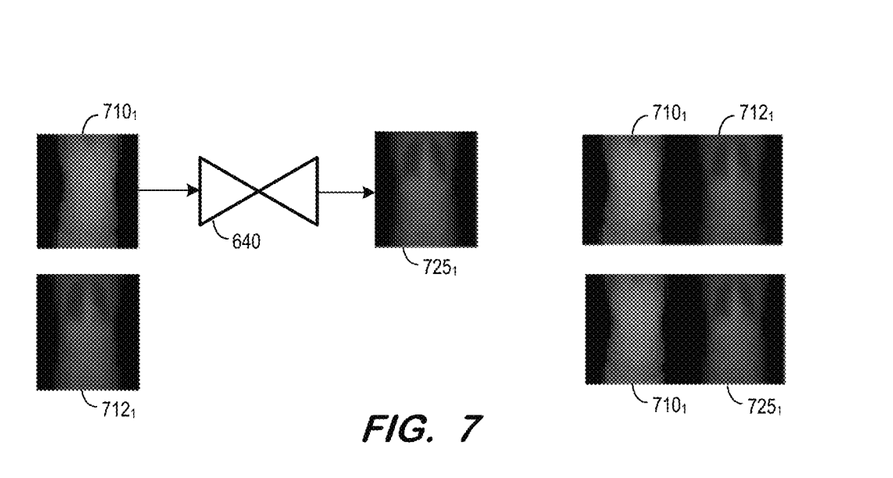
FIG. 7 is a block diagram illustrating generation of training data for a descriptor network according to some embodiments.

The trained CT data generation network is used at S230 to generate CT data based on ground truth surface data. FIG. 7 illustrates generation of CT data at S230 according to some embodiments. Ground truth surface data $710_1$ is input to trained CT generation network 640, which outputs generated CT data $725_1$. Also shown is ground truth CT data $712_1$, resulting from an actual CT scan and from which surface data $710_1$ was determined. As shown to the right of FIG. 7, a first ground truth stacked image is created including ground truth images $710_1$ and $712_1$, and a second stacked image is created including the ground truth image $710_1$ and generated CT image $725_1$. This process repeats to create two stacked images for each of many more sets of ground truth surface data instances $710_{2\to n}$ and ground truth CT data instances $712_{2\to n}$.

Figure 8:
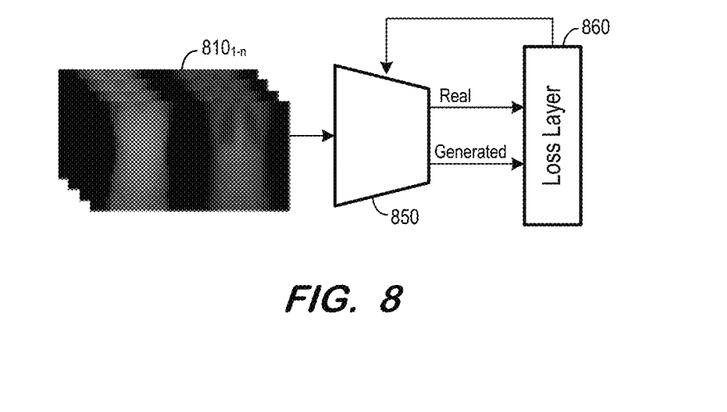
FIG. 8 is a block diagram illustrating training of a descriptor network according to some embodiments.

The stacked images generated at S230 are used to train a discriminator network at S240. Discriminator network 850 of FIG. 8 receives stacked images comprising surface data and CT data, and determines whether the CT data is real (i.e., ground truth") or generated by generator 640. Loss layer 860 compares the results of the determination with the true nature of each stacked image and back-propagates a corresponding loss value to network 850. Network 850 is modified based on the loss value and the process continues until a satisfactory performance level is achieved.

Figure 9:
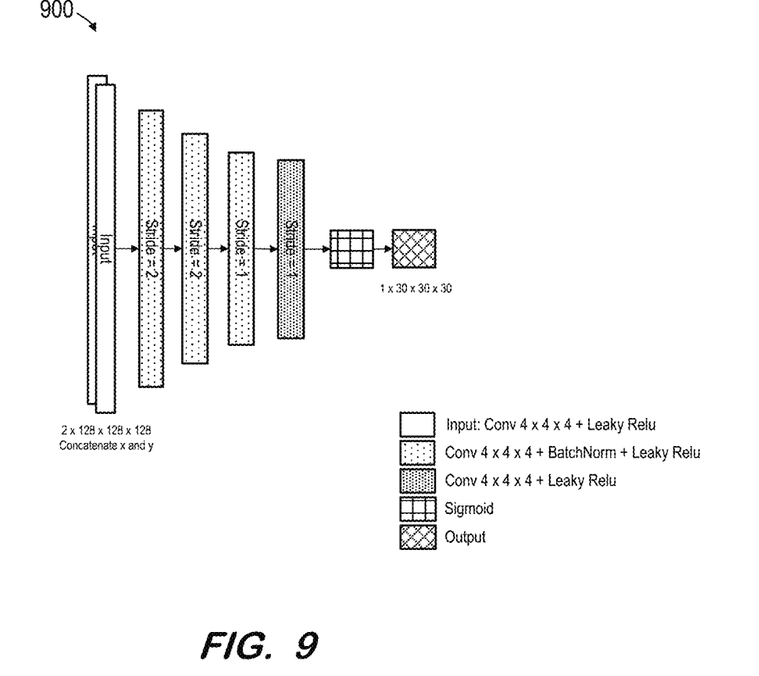
FIG. 9 illustrates a descriptor network architecture according to some embodiments.

FIG. 9 illustrates architecture 900 of discriminator 850 according to some embodiments. Architecture 900 employs a PatchGAN classifier, which penalizes structure at the scale of image patches. According to some embodiments, the receptive field of architecture 900 is thirty-four and the output size is 30×30×30. Embodiments are not limited to architecture 900.

Each of the regression, generator and discriminator networks discussed herein may be implemented by a computing system as is known in the art. Such a computing system may include one or more processing units which execute processor-executable process steps to create data structures representing layers of each network and the interconnections therebetween, to receive input data and process the input data based on the layers, to determine loss based on an output, and to modify the network based on the loss. Such a computing system may include a storage device to store the data structures and training data instances.

Figure 10:
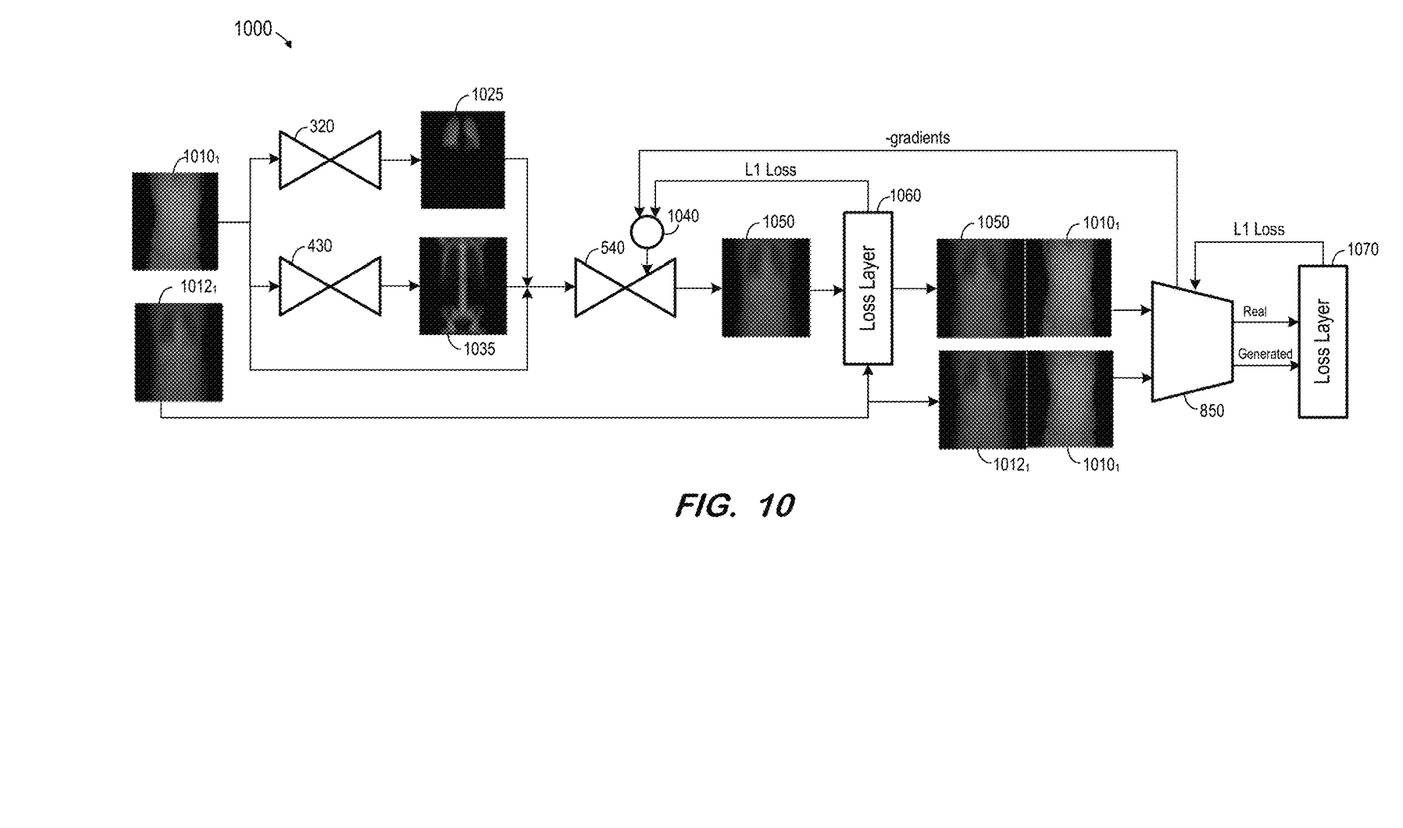
FIG. 10 is a block diagram illustrating training using dual-conditional generative adversarial networks according to some embodiments.

FIG. 10 illustrates end-to-end network training architecture 1000 according to some embodiments. Architecture 1000 is a novel implementation of a dual-conditional generative adversarial network training architecture. Generally, the CT data generator is optimized based on multiple objectives, and additional constraints are enforced by adding losses on intermediate outputs instead of directly regressing the output from the input.

Figure 11:
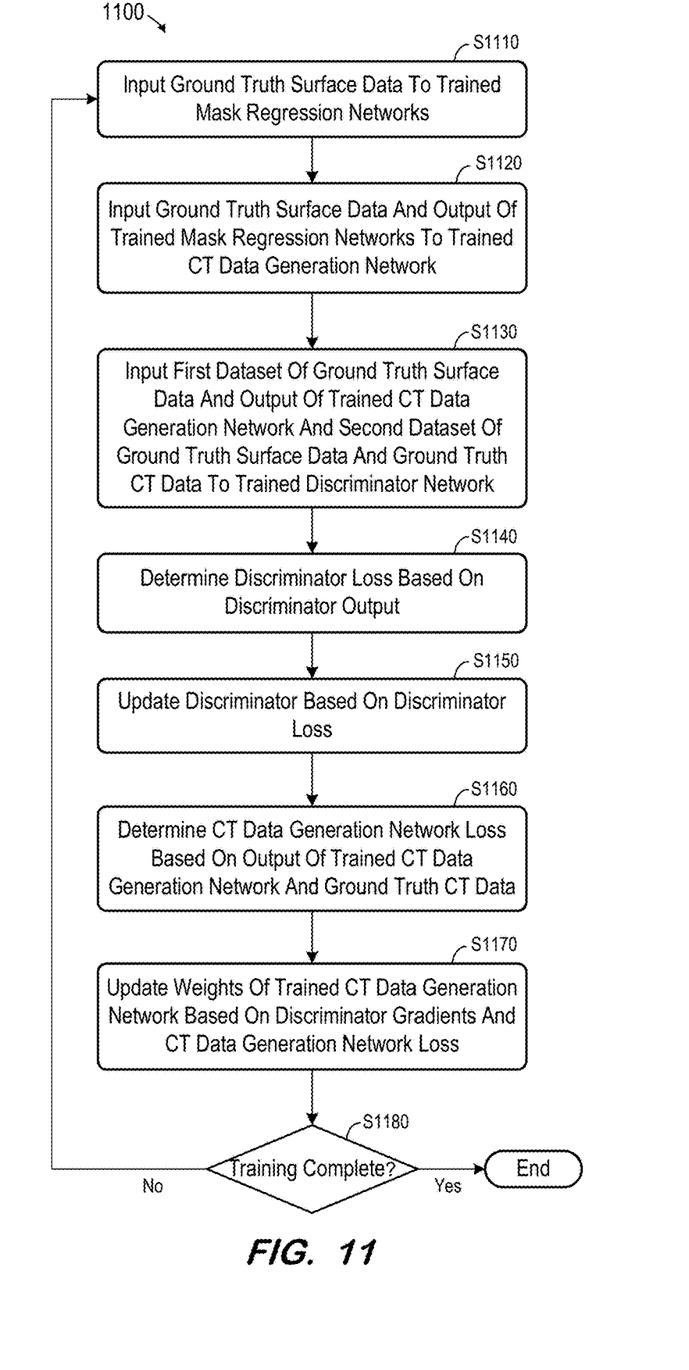
FIG. 11 is a flow diagram of training using dual-conditional generative adversarial networks according to some embodiments.

Process 1100 describes the operation of architecture 1000 according to some embodiments. Initially, at S1110, ground truth surface data is input to the mask regression networks trained at S210 of process 200. As shown in FIG. 10, ground truth surface data $1010_1$ is input to trained lung mask regression network 320 and to trained bone mask regression network 430. Consequently, lung mask regression network 320 outputs lung mask 1025 and bone mask regression network 430 outputs bone mask 1035.

The ground truth surface data and the outputs of the trained mask regression networks are input to the trained CT data generation network at S1120. In the present example, trained CT data generation network 540 outputs generated CT data 1050 after S1120.

Next, at S1130, a first dataset and a second dataset are input to the trained discriminator network. The first dataset includes the ground truth surface data and the output of the trained CT generation network and the second dataset includes the ground truth surface data and the ground truth CT data. These datasets are depicted in FIG. 10 as being input to trained discriminator 850. In response, the discriminator generates output identifying one of the datasets as real (i.e., ground truth) and one of the datasets as generated.

A discriminator loss is determined at S1140 based on the discriminator output. In some embodiments, loss layer 1070 determines the loss based on whether discriminator 850 correctly identifies the real CT dataset and the generated CT dataset. The loss is back-propagated and the discriminator is updated based thereon at S1150 as is known in the art.

CT generation network loss is determined at S1160 (e.g., by loss layer 1060) based on the output of the CT data generation network (e.g., CT data 1050), the ground truth CT data (e.g., ground truth CT data $1012_1$) and the output of the discriminator. The CT generation network loss is the weighted sum of the reconstruction loss and the adversarial loss determined by the discriminator output. The reconstruction loss is pixel-wise mean squared error between the output of the CT data generation network (e.g., CT data 1050) and the ground truth CT data (e.g., ground truth CT data $1012_1$). The total loss is back-propagated and the generator network is updated at S1170. Backpropagating the loss to update the generator network involves computing the gradients from the loss, and modifying the network weights using the computed gradients. For updating the CT generation network, the gradients are computed by a weighted sum of the gradients from the backpropagation of the reconstruction loss and the negative of the gradients from the backpropagation of the discriminator.

Accordingly, during training, changes made to discriminator 850 due to classification loss are used to influence changes made to generation network 540. The changes made to generation network 540 are therefore in response to adversarial loss and reconstruction loss. As a result, generation network 540 is trained to achieve two goals: to minimize loss and to increase the error rate of discriminator 850.

At S1180, it is determined whether the training is complete. This determination may be based on elapsed time, number of iterations, performance level, the availability of training samples, and/or any other suitable metric. If it is determined that training is not yet complete, flow returns to S1110 to input another ground truth surface data. If not, then the thusly-trained mask regression networks and CT data generation networks may be deployed as shown in FIG. 1 to predict CT data based on input surface data. In such a deployment, the input surface data may be data acquired by a depth scanner, for example, or CT surface data which is generated based on data acquired by a depth scanner.

Figure 12:
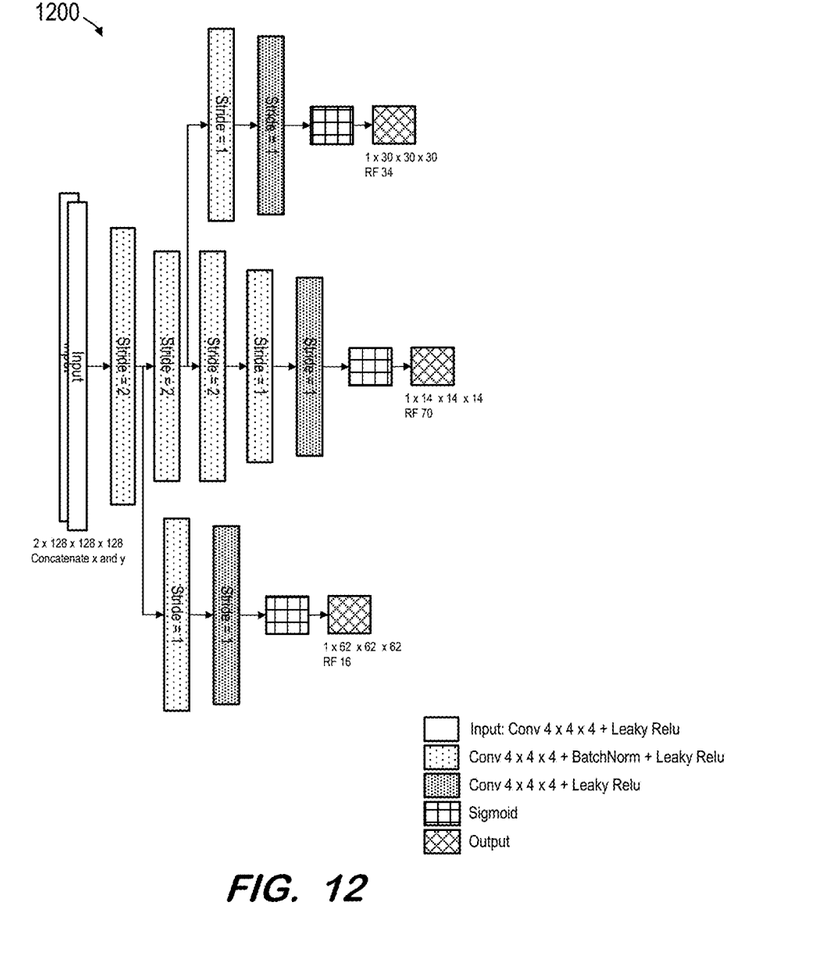
FIG. 12 illustrates a descriptor network architecture according to some embodiments.

Discriminator architecture 900 computes loss at one scale, by processing a two-channel input image through a deep network and computing the loss at the output layer. This approach may summarize features at a particular scale. FIG. 12 depicts architecture 1200 of a discriminator to evaluate image content at multiple scales according to some embodiments. For example, at a coarser scale, architecture 1200 attempts to ensure that larger structures such as a lung, pelvis or heart correlate well with the input, and to ensure at a finer scale that the spine structure and ribs are also well-captured. The overall discriminator loss may be determined at S1150 as a weighted sum of the individual losses, for example using weights of 0.4, 0.3 and 0.4, respectively.

Figure 13:
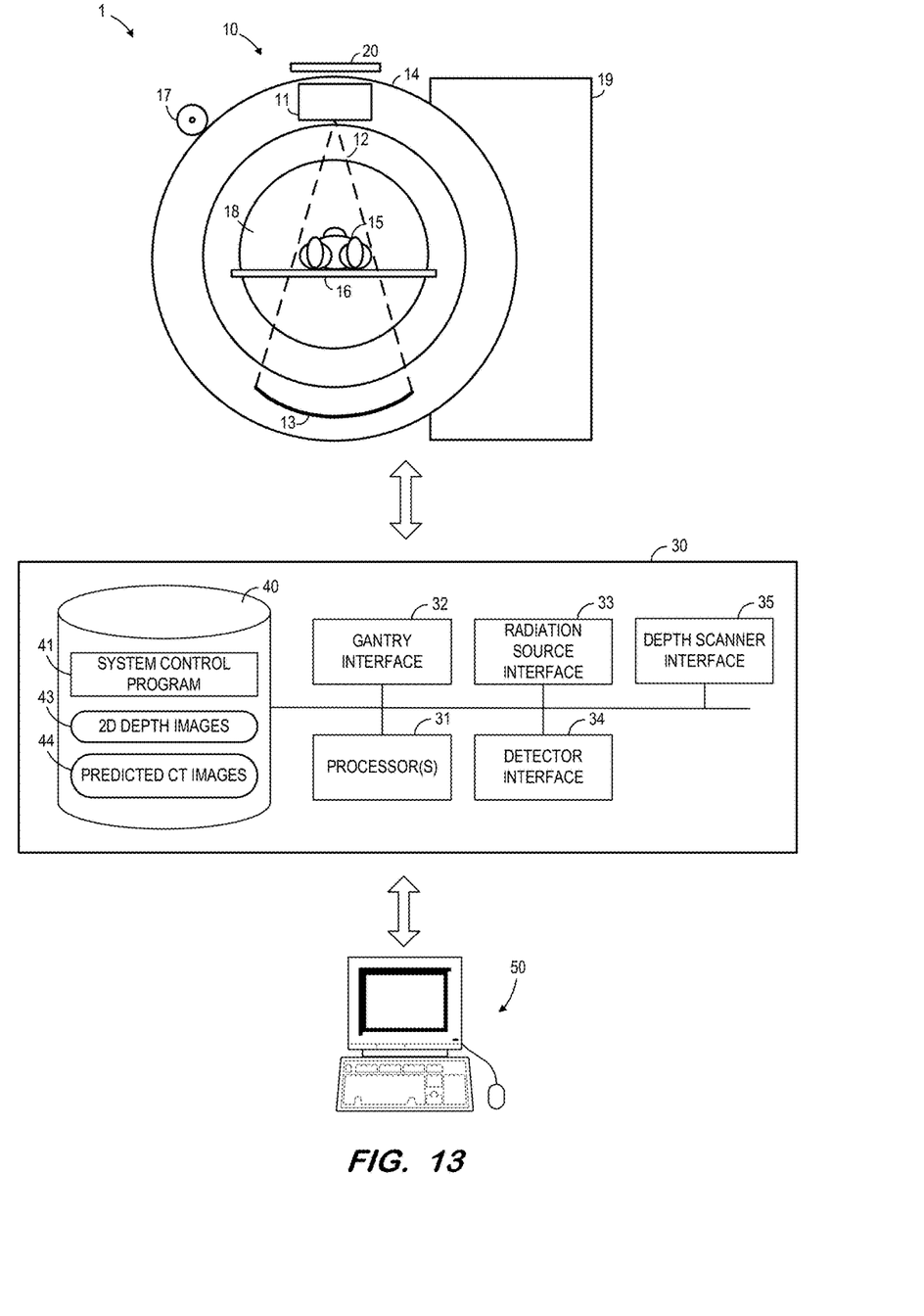
FIG. 13 illustrates an imaging system according to some embodiments.

FIG. 13 illustrates system 1 according to some embodiments. System 1 may be operated to acquire surface data and predict CT data based on the surface data according to some embodiments. Embodiments are not limited to system 1 to perform either function.

System 1 includes X-ray imaging system 10, scanner 20, control and processing system 30, and operator terminal 50. Generally, and according to some embodiments, X-ray imaging system 10 acquires two-dimensional X-ray images of a patient and scanner 20 acquires surface data of the patient. Control and processing system 30 controls X-ray imaging system 10 and scanner 20, and receives the acquired images therefrom. Control and processing system 30 processes the surface data to predict CT data as described above. Such processing may be based on user input received by terminal 50 and provided to control and processing system 30 by terminal 50.

Imaging system 10 comprises a CT scanner including X-ray source 11 for emitting X-ray beam 12 toward opposing radiation detector 13. Embodiments are not limited to CT data or to CT scanners. X-ray source 11 and radiation detector 13 are mounted on gantry 14 such that they may be rotated about a center of rotation of gantry 14 while maintaining the same physical relationship therebetween.

Radiation detector 13 may comprise any system to acquire an image based on received X-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

To generate X-ray images, patient 15 is positioned on bed 16 to place a portion of patient 15 between X-ray source 11 and radiation detector 13. Next, X-ray source 11 and radiation detector 13 are moved to various projection angles with respect to patient 15 by using rotation drive 17 to rotate gantry 14 around cavity 18 in which patient 15 is positioned. At each projection angle, X-ray source 11 is powered by high-voltage generator 19 to transmit X-ray radiation 12 toward detector 13. Detector 13 receives the radiation and produces a set of data (i.e., a raw X-ray image) for each projection angle.

Scanner 20 may comprise a depth camera. Scanner 20 may acquire image data which consists of a two-dimensional image (e.g., a two-dimensional RGB image, in which each pixel is assigned a Red, a Green and a Blue value), and a depth image, in which the value of each pixel corresponds to a depth or distance of the pixel from the depth camera. This image data, consisting of a two-dimensional image and a depth image, is referred to herein as a two-dimensional depth image. Scanner 20 may comprise a structured light-based camera, a stereo camera, or a time-of-flight camera according to some embodiments.

System 30 may comprise any general-purpose or dedicated computing system. Accordingly, system 30 includes one or more processors 31 configured to execute processor-executable program code to cause system 30 to operate as described herein, and storage device 40 for storing the program code. Storage device 40 may comprise one or more fixed disks, solid-state random access memory, and/or removable media (e.g., a thumb drive) mounted in a corresponding interface (e.g., a USB port).

Storage device 40 stores program code of system control program 41. One or more processors 31 may execute system control program 41 to move gantry 14, to move table 16, to cause radiation source 11 to emit radiation, to control detector 13 to acquire an image, to control scanner 20 to acquire an image, and to perform any other function. In this regard, system 30 includes gantry interface 32, radiation source interface 33 and depth scanner interface 35 for communication with corresponding units of system 10.

System control program 41 may also be executable to implement trained mask regression and CT data generation networks as described herein. Accordingly, one or more processors 31 may execute system control program 41 to receive surface data and to generate predicted CT images therefrom.

Device 40 stores two-dimensional depth images 43 acquired by scanner 20. Two-dimensional depth images 43 may comprise surface data as described herein. In some embodiments, CT surface data is generated based on two-dimensional depth images 43 and the generated CT surface data is input to trained networks as described herein to generate predicted CT images. In this regard, device 40 also stores predicted CT images 44. As described above, predicted CT images 44 may be used to position patient 15, to plan subsequent imaging or treatment, or for any other purpose for which conventional CT images are used.

Terminal 50 may comprise a display device and an input device coupled to system 30. Terminal 50 may display any of two-dimensional depth images 43 and predicted CT images 44, and may receive user input for controlling display of the images, operation of imaging system 10, and/or the processing described herein. In some embodiments, terminal 50 is a separate computing device such as, but not limited to, a desktop computer, a laptop computer, a tablet computer, and a smartphone.

Each of system 10, scanner 20, system 30 and terminal 40 may include other elements which are necessary for the operation thereof, as well as additional elements for providing functions other than those described herein.

According to the illustrated embodiment, system 30 controls the elements of system 10. System 30 also processes images received from system 10. Moreover, system 30 receives input from terminal 50 and provides images to terminal 50. Embodiments are not limited to a single system performing each of these functions. For example, system 10 may be controlled by a dedicated control system, with the acquired frames and images being provided to a separate image processing system over a computer network or via a physical storage medium (e.g., a DVD).

Embodiments are not limited to a CT scanner and an RGB+D scanner as described above. For example, embodiments may employ any other imaging modalities (e.g., a magnetic resonance scanner, a positron-emission scanner, etc.) for acquiring surface data.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
    a storage device storing a plurality of sets of data, each of the plurality of sets of data comprising an instance of surface data and a corresponding instance of computed tomography data;
    a processor to execute processor-executable process steps to cause the system to:
        operate a generation network to generate first generated computed tomography data based on a first instance of surface data of a first set of data;
        determine a generation loss based on the first generated computed tomography data and on a first instance of computed tomography data of the first set of data and corresponding to the first instance of surface data;
        operate a discriminator network to discriminate between the first generated computed tomography data and the first instance of computed tomography data;
        determine a discriminator loss based on the discrimination between the first generated computed tomography data and the first instance of computed tomography data;
        determine discriminator gradients of the discriminator network based on the discriminator loss; and
        update weights of the generation network based on the generation loss and the discriminator gradients.

2. The system according to claim 1, wherein the processor further executes processor-executable process steps to cause the system to:
    operate the generation network based on the updated weights to generate second generated computed tomography data based on a second instance of surface data of a second set of data;
    determine a second generation loss based on the second generated computed tomography data and on a second instance of computed tomography data of the second set of data and corresponding to the second instance of surface data;
    operate the discriminator network based on the determined discriminator gradients to discriminate between the second generated computed tomography data and the second instance of computed tomography data;
    determine a second discriminator loss based on the discrimination between the second generated computed tomography data and the second instance of computed tomography data;
    determine second discriminator gradients of the discriminator network based on the second discriminator loss; and
    update weights of the generation network based on the second generation loss and the second discriminator gradients.

3. The system according to claim 1, wherein each of the plurality of sets of data comprises an instance of surface data, a corresponding instance of computed tomography data, and a corresponding instance of a bone mask, and
    wherein operation of the generation network to generate the first generated computed tomography data is based on the first instance of surface data of the first set of data and on a first instance of a bone mask of the first set of data.

4. The system according to claim 1, wherein each of the plurality of sets of data comprises an instance of surface data, a corresponding instance of computed tomography data, a corresponding instance of a bone mask, and a corresponding instance of a lung mask, and
    wherein operation of the generation network to generate the first generated computed tomography data is based on the first instance of surface data of the first set of data, on a first instance of a bone mask of the first set of data, and on a first instance of a lung mask of the first set of data.

5. The system according to claim 4, wherein the processor further executes processor-executable process steps to cause the system to:
    operate the generation network based on the updated weights to generate second generated computed tomography data based on a second instance of surface data of a second set of data, on a second instance of a bone mask of the second set of data, and on a second instance of a lung mask of the first set of data;
    determine a second generation loss based on the second generated computed tomography data and on a second instance of computed tomography data of the second set of data and corresponding to the second instance of surface data;

operate the discriminator network based on the determined discriminator gradients to discriminate between the second generated computed tomography data and the second instance of computed tomography data;

determine a second discriminator loss based on the discrimination between the second generated computed tomography data and the second instance of computed tomography data;

determine second discriminator gradients of the discriminator network based on the second discriminator loss; and update weights of the generation network based on the second generation loss and the second discriminator gradients.

6. The system according to claim 1, wherein operation of the discriminator network to discriminate between the first generated computed tomography data and the first instance of computed tomography data comprises:

operation of the discriminator network to discriminate between the first generated computed tomography data and the first instance of computed tomography data at a first scale and to discriminate between the first generated computed tomography data and the first instance of computed tomography data at a second scale, and wherein determination of the discrimination loss comprises:

determination of a first discrimination loss based on the discrimination between the first generated computed tomography data and the first instance of computed tomography data at the first scale;

determination of a second discrimination loss based on the discrimination between the first generated computed tomography data and the first instance of computed tomography data at the second scale; and determination of the discrimination loss based on the first discrimination loss and the second discrimination loss.

7. The system according to claim 6, wherein each of the plurality of sets of data comprises an instance of surface data, a corresponding instance of computed tomography data, a corresponding instance of a bone mask, and a corresponding instance of a lung mask, and wherein operation of the generation network to generate the first generated computed tomography data is based on the first instance of surface data of the first set of data, on a first instance of a bone mask of the first set of data, and on a first instance of a lung mask of the first set of data.

8. A computer-implemented method, comprising:

operating a generation network to generate first generated computed tomography data based on a first instance of surface data;

determining a generation loss based on the first generated computed tomography data and on a first instance of computed tomography data which corresponds to the first instance of surface data;

operating a discriminator network to discriminate between the first generated computed tomography data and the first instance of computed tomography data;

determining a discriminator loss based on the discrimination between the first generated computed tomography data and the first instance of computed tomography data;

determining discriminator gradients of the discriminator network based on the discriminator loss; and updating weights of the generation network based on the generation loss and the discriminator gradients.

9. The method according to claim 8, further comprising:

operating the generation network based on the updated weights to generate second generated computed tomography data based on a second instance of surface data;

determining a second generation loss based on the second generated computed tomography data and on a second instance of computed tomography data which corresponds to the second instance of surface data;

operating the discriminator network based on the determined discriminator gradients to discriminate between the second generated computed tomography data and the second instance of computed tomography data;

determining a second discriminator loss based on the discrimination between the second generated computed tomography data and the second instance of computed tomography data;

determining second discriminator gradients of the discriminator network based on the second discriminator loss; and updating weights of the generation network based on the second generation loss and the second discriminator gradients.

10. The method according to claim 8, wherein operating the generation network to generate the first generated computed tomography data is based on the first instance of surface data and on a first instance of a bone mask which corresponds to the first instance of surface data.

11. The method according to claim 8, wherein operating the generation network to generate the first generated computed tomography data is based on the first instance of surface data, on a first instance of a bone mask which corresponds to the first instance of surface data, and on a first instance of a lung mask which corresponds to the first instance of surface data.

12. The method according to claim 11, further comprising:

operating the generation network based on the updated weights to generate second generated computed tomography data based on a second instance of surface data, on a second instance of a bone mask which corresponds to the second instance of surface data, and on a second instance of a lung mask which corresponds to the second instance of surface data;

determining a second generation loss based on the second generated computed tomography data and on a second instance of computed tomography data which corresponds to the second instance of surface data;

operating the discriminator network based on the determined discriminator gradients to discriminate between the second generated computed tomography data and the second instance of computed tomography data;

determining a second discriminator loss based on the discrimination between the second generated computed tomography data and the second instance of computed tomography data;

determining second discriminator gradients of the discriminator network based on the second discriminator loss; and updating weights of the generation network based on the second generation loss and the second discriminator gradients.

13. The method according to claim 8, wherein operating the discriminator network to discriminate between the first generated computed tomography data and the first instance of computed tomography data comprises:
   operating the discriminator network to discriminate between the first generated computed tomography data and the first instance of computed tomography data at a first scale and to discriminate between the first generated computed tomography data and the first instance of computed tomography data at a second scale, and
   wherein determining the discrimination loss comprises:
   determining a first discrimination loss based on the discrimination between the first generated computed tomography data and the first instance of computed tomography data at the first scale;
   determining a second discrimination loss based on the discrimination between the first generated computed tomography data and the first instance of computed tomography data at the second scale; and
   determining the discrimination loss based on the first discrimination loss and the second discrimination loss.

14. The method according to claim 13, wherein operating the generation network to generate the first generated computed tomography data is based on the first instance of surface data, on a first instance of a bone mask which corresponds to the first instance of surface data, and on a first instance of a lung mask which corresponds to the first instance of surface data.

15. A non-transitory computer-readable medium storing processor-executable process steps, the process steps executable by a processor to cause a system to:
   operate a generation network to generate first generated computed tomography data based on a first instance of surface data;
   determine a generation loss based on the first generated computed tomography data and on a first instance of computed tomography data which corresponds to the first instance of surface data;
   operate a discriminator network to discriminate between the first generated computed tomography data and the first instance of computed tomography data;
   determine a discriminator loss based on the discrimination between the first generated computed tomography data and the first instance of computed tomography data;
   determine discriminator gradients of the discriminator network based on the discriminator loss; and
   update weights of the generation network based on the generation loss and the discriminator gradients.

16. The non-transitory computer-readable medium according to claim 15, the process steps executable by the processor to further cause the system to:
   operate the generation network based on the updated weights to generate second generated computed tomography data based on a second instance of surface data;
   determine a second generation loss based on the second generated computed tomography data and on a second instance of computed tomography data which corresponds to the second instance of surface data;
   operate the discriminator network based on the determined discriminator gradients to discriminate between the second generated computed tomography data and the second instance of computed tomography data;
   determine a second discriminator loss based on the discrimination between the second generated computed tomography data and the second instance of computed tomography data;
   determine second discriminator gradients of the discriminator network based on the second discriminator loss; and
   update weights of the generation network based on the second generation loss and the second discriminator gradients.

17. The non-transitory computer-readable medium according to claim 15, wherein operation of the generation network to generate the first generated computed tomography data is based on the first instance of surface data and on a first instance of a bone mask which corresponds to the first instance of surface data.

18. The non-transitory computer-readable medium according to claim 15, wherein operation of the generation network to generate the first generated computed tomography data is based on the first instance of surface data, on a first instance of a bone mask which corresponds to the first instance of surface data, and on a first instance of a lung mask which corresponds to the first instance of surface data.

19. The non-transitory computer-readable medium according to claim 18, the process steps executable by the processor to further cause the system to:
   operate the generation network based on the updated weights to generate second generated computed tomography data based on a second instance of surface data, on a second instance of a bone mask which corresponds to the second instance of surface data, and on a second instance of a lung mask which corresponds to the second instance of surface data;
   determine a second generation loss based on the second generated computed tomography data and on a second instance of computed tomography data which corresponds to the second instance of surface data;
   operate the discriminator network based on the determined discriminator gradients to discriminate between the second generated computed tomography data and the second instance of computed tomography data;
   determine a second discriminator loss based on the discrimination between the second generated computed tomography data and the second instance of computed tomography data;
   determine second discriminator gradients of the discriminator network based on the second discriminator loss; and
   update weights of the generation network based on the second generation loss and the second discriminator gradients.

20. The non-transitory computer-readable medium according to claim 15, wherein operation of the discriminator network to discriminate between the first generated computed tomography data and the first instance of computed tomography data comprises:
   operation of the discriminator network to discriminate between the first generated computed tomography data and the first instance of computed tomography data at a first scale and to discriminate between the first generated computed tomography data and the first instance of computed tomography data at a second scale, and
   wherein determination of the discrimination loss comprises:
   determination of a first discrimination loss based on the discrimination between the first generated computed tomography data and the first instance of computed tomography data at the first scale;
   determination of a second discrimination loss based on the discrimination between the first generated computed tomography data and the first instance of computed tomography data at the second scale; and
determination of the discrimination loss based on the first discrimination loss and the second discrimination loss.

* * * * *